United States Patent [19]

Ball

[11] Patent Number: 4,971,434
[45] Date of Patent: Nov. 20, 1990

[54] METHOD FOR DIAGNOSING DEFICIENCIES IN AND EXPANDING A PERSON'S USEFUL FIELD OF VIEW

[75] Inventor: Karlene K. Ball, Bowling Green, Ky.

[73] Assignee: Visual Resources, Inc., Bowling Green, Ky.

[21] Appl. No.: 441,992

[22] Filed: Nov. 28, 1989

[51] Int. Cl.$^5$ .............................................. A61B 3/02
[52] U.S. Cl. .................................... 351/224; 351/226
[58] Field of Search ................ 351/222, 224, 226, 203

[56] References Cited

U.S. PATENT DOCUMENTS 4,685,784  8/1987  Kirchhuebel ....................... 351/224

OTHER PUBLICATIONS

Report entitled "Vision Assessment Technology and the Screening of Older Drivers", Frank Schieber, Ph.D., Feb., 1988.
Appendix: U.S. Department of Transportation's Research Initiative, Frank Schieber, Ph.D., 1988.
"Pattern Discrimination Perimetry: A New Concept in Visual Field Testing," 7th Int'l Visual Field Supposium (1987), B. Drum et al.
Article entitled "Age and Visual Search: Expanding the Useful Field of View," 12/1988.
Article entitled "Visual Localization: Age and Practice," J. Opt. Soc. Am., vol. 3, No. 6, (Robert Secular and Karlene Ball), Jun. 1986.

Primary Examiner—Paul M. Dzierzynski
Attorney, Agent, or Firm—Leydig, Voit & Mayer

[57] ABSTRACT

A method for diagnosing deficiencies in and expanding the size of a person's "Useful Field Of View" (UFOV). The UFOV is determined by the eccentricity (in degrees of visual angle) at which peripheral targets (presented within an embedding context) can be localized 50% of the time while performing a concurrent visual task in central vision. The method provides multiple blocks of trials, each block of trials consists of displaying a plurality of times before a subject's vision a set of four sequentially presented images having specific characteristics, and the specific characteristics of each block of trials is changed each time a new block of trials is displayed before the subject. By changing the characteristics of each block of trials, a diagnosis can be made of the subject's vision by creating a subject database that contains the subject's indicated responses to each block of trials having specific characteristics and comparing the subject database to a normative diagnostic database in order to achieve a diagnosis. The method also employs training programs to expand the size of the subject's UFOV.

10 Claims, 8 Drawing Sheets

FIXATION BOX

STIMULUS

MASK

RESPONSE GRID

METHOD FOR DIAGNOSING DEFICIENCIES IN AND EXPANDING A PERSON'S USEFUL FIELD OF VIEW

FIELD OF THE INVENTION

The present invention relates generally to automated visual testing devices, and more particularly to diagnosing deficiencies in expanding a person's useful field of view.

BACKGROUND OF THE INVENTION

Ophthalmologists and optometrists are sometimes called upon to evaluate the functional status of the visual system in terms of what activities an individual may engage in, in addition to diagnosing the presence of pathology. Requests for this kind of diagnosis may come from different sources such as government (disability payments), employers (meeting standards for employment) or state departments of motor vehicles (driving status). These types of evaluations may prove a difficult task since there is often a mismatch between sensory loss and the ability to function in the world—i.e., some individuals with dramatic sensory loss seem to function quite well while others, with only minor sensory loss, report great difficulty in visually guided activities. This difficulty may be exacerbated in the older population, where there is a marked increase in the range of functional disabilities, and often no clear distinction between aging and early onset of disease. Therefore, tests of functional vision are needed so evaluations can be made fairly, rather than based on age alone or on sensory tests alone which tend to be unrelated to behavioral measures.

Many different kinds of perimeters are available for assessing the integrity of the clinical visual field. Existing automated perimeters are used to screen for the presence of pathology (i.e., glaucoma or retinal damage), and may also be used to provide full threshold determination for many points throughout the visual field. These perimeters may employ projection techniques (for example, the Octopus Perimeter 500EZ by Interzeag Inc., Northboro, Mass. 01532) or use LED stimuli as targets, and can vary the backgrounds luminance, stimulus size and the exposure time of the targets. The software provided with these perimeters allows brief screening tests, a full threshold test, customized testing, electronic fixation monitoring with video cameras, an indication of short-term fluctuations, a comparison of thresholds obtained with normal values corrected for age, defect analysis, and tracking for visual field indices over time.

In comparison to these clinical visual fields, the useful field of view (UFOV) has been defined as the spatial area or visual field extent that is needed for a specific visual task. Unlike the traditional field, the UFOV is measured binocularly, employs suprathreshold rather than threshold targets, and both the target and background are complex. Although age-related deficits occur for both the clinical measures of the visual field, as obtained with standard perimetry and UFOV assessments, agerelated declines tend to be much larger for the UFOV measurements.

In addition to screening for pathology, standard perimetry has also been employed as a screening device for various behavioral measures such as driving. All research in this area has failed to find a relationship between the status of the visual field and difficulty in driving (as assessed by accident rate) except in a very small percentage of drivers with severe binocular field loss. Additionally, clinical visual field measures have not been found to be predictive of reported difficulties on visual tasks relating to visual search, mobility and speed of visual processing (as assessed by survey responses). Measures of the UFOV, however, are predictive of such reported difficulties. Thus, standard perimetric techniques underestimate the severity of many adults functional loss in the visual field. While older adults typically show some slight sensitivity losses throughout the visual field (relative to young adults), assessment of the UFOV can reveal up to a three-fold reduction in the field. Thus assessment of the UFOV could be used to delineate the perceptual functions necessary for the performance of routine activities dependent on vision, such as driving. In addition, expansion of the UFOV through training could improve the level of visually functioning ability for both young and old adults.

In order to attract a person's visual attention, objects or visual stimuli must be salient or conspicuous against their background. The UFOV provides a measure of how well peripheral targets can alert the attentional system (i.e., draw a person's attention) to relevant information or events in a person's environment. There is a tradeoff between the duration of stimulus presentation and the size of the area in which the visual system can be alerted. Individuals with a smaller UFOV are at a disadvantage in terms of their ability to quickly re-orient their attention (for example, to a vehicle approaching from the side) because they will not perceive its approach until it is much closer than it would have to be for an individual with a larger UFOV. Thus individuals with a smaller UFOV, in order to attend to the same visual area, would require more visual fixations (eye movements) and each fixation would need to be of a longer durational time period. It is as if their window of visibility was two to three times smaller than that of an individual without this type of problem.

SUMMARY OF THE INVENTION

In view of the foregoing, it is the primary object of the invention to provide a method for diagnosing deficiencies in and expanding the UFOV. This method can be implemented in an automated visual perimeter device.

Standard clinical perimeters were not originally intended to assess functional vision and seek to minimize many of the components of everyday vision (targets within a context, simultaneous use of both foveal and peripheral vision, distractions, uncertainty of target location, and suprathreshold stimuli). By way of contrast, the measure of the UFOV via the present method is designed to simulate everyday demands on the visual system. The method can thus be used to improve or supplement ophthalmic examinations, as well as predict functional vision abilities in various everyday activities.

Briefly, the method provides multiple blocks of trials, each block of trials consists of displaying a plurality of times before a subject's vision a set of four sequentially presented images having specific characteristics, and the specific characteristics of each block of trials is changed each time a new block of trials is displayed before the subject. By changing the characteristics of each block of trials, a diagnosis can be made of the subject's vision by creating a subject database that contains the subject's indicated responses to each block of trials having specific characteristics and comparing the subject database to a normative (or standardized) diagnostic database in order to achieve a diagnosis, and then from that diagnosis map out a training routine, if necessary. The diagnostic database contains standardized responses for each block of trials having specific characteristics. The varying characteristics of each block of trials consists of changing the duration period of the images displayed and the discerning or distinguishing difficulty of the foveal or peripheral images displayed. Each block of trials having specific characteristics consists of displaying a plurality of times the set of four sequentially presented images. Each time this set of four sequentially presented images is displayed in a block of trials having specific characteristics, the details and locations of features in the presented images are changed.

The first image of each set of four sequentially presented images is a fixation box which localizes the subject's acute or foveal vision. The second image of each set contains a figure having variable details located in the center of the fixation box and distractor figures peripherally located around the foveal or center figure at differing "eccentricities." In the context of the present invention, the word "eccentricity" is the angle in degrees from the point of visual fixation to a target image as measured from the position of the subject. The second image is only displayed for a brief period of time. During that period, however, the subject must localize the peripheral target image while simultaneously concentrating on the changing details of the center figure. The third image displayed is a masking image to prevent afterimages on the subject's retina or on the display means. The fourth image is a prompt requesting the subject to indicate the details of the center figure and direction of the unique peripheral figure in relation to the center figure.

While the present method for diagnosing deficiencies in and expanding a subject's UFOV will be described in connection with a preferred embodiment, there is no intent to limit it to that embodiment. On the contrary, the intent is to cover all alternatives, modifications and equivalences included within the spirit and the scope of the method as defined by the appended claims.

DETAILED DESCRIPTION OF THE PREFERRED EMBODIMENT

Figure 1:
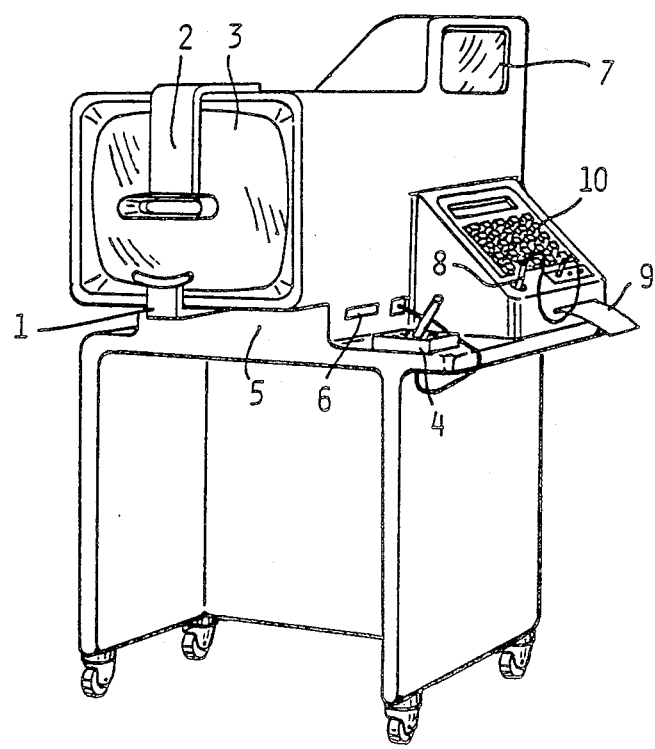
FIG. 1 is a perspective view of a preferred vision testing device implementing the present method.

Turning to the drawings and referring first to FIG. 1, the preferred testing device implementing the present method for diagnosing deficiencies in and expanding a subject's UFOV is illustrated. A chin rest 1 and head rest 2 are provided for positioning a subject's head a specific distance from the subject monitor 3 and in the middle of the screen. The subject monitor 3 is preferably a 20 inch diagonal multisync color monitor (model SD) controlled via a VGA card and CPU system with a 1280 by 1024 resolution. A joystick 4 is provided for the subject to input responses of the status of the displayed images of the present method.

In a preferred embodiment of the vision testing device implementing the present method, the CPU 5 will be a 80286 CPU system (Western Digital AT 12.5 MHz motherboard with Pheonix Bios). This includes a 512K memory plus 32K cache memory, 2serial ports, one parallel port, one mouse port and a 200 watt power supply. Also included is a Western Digital WD-1006 floppy hard controller and a 1.2 MB floppy drive 6.

The system operator may use an input device, such as a light pen 8 and an operator monitor 7, to initialize the program, select options, and respond to questions presented on the operator monitor 7. The system operator may also input data via keyboard 10. A paper printout 9 of the test results will be produced after each test sequence is completed.

FIG. 2 illustrates the set of four sequentially displayed images having variable characteristics which are displayed on the subject monitor 3. Initially, a fixation box 2a appears for approximately two seconds. This is followed by a brief display of visual stimulus 2b. Stimuli are displayed in twenty-four possible positions at each of three eccentricities and along eight radial lines. For example, in the illustrated stimulus 2b a subject will be asked to discern whether foveal image 12 (in this case a face) displayed within the fixation box 11 was happy or sad (in this case sad), and would also have to respond to the location of peripheral target 13 (in this case a face) embedded in box distractors by selecting one of the eight designated radial locations via the joystick 4. Display 2c illustrates the masking stimulus of the present method used to erase possible ghost images on the subject monitor 3 and prevent afterimages on the subject's retina. Finally, the fourth image of present method, FIG. 2d, is displayed showing the eight possible radial choices from which the subject is to select as the correct location of the peripheral target 13. FIG. 2d will remain on the subject monitor 3 until the subject responds.

Figure 3A:
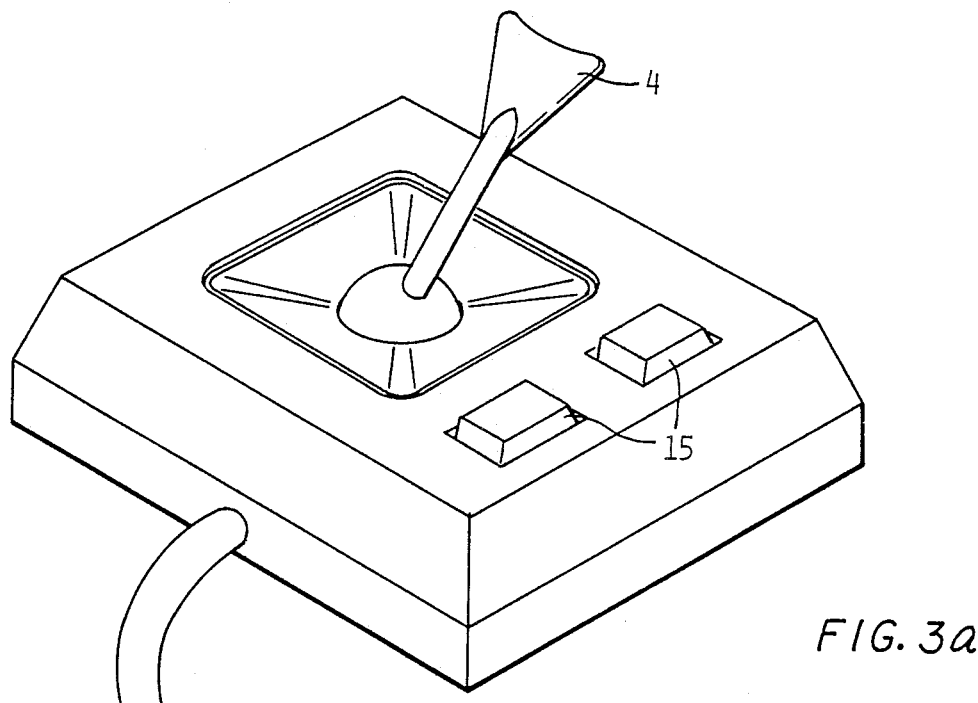
FIG. 3 is a view illustrating the specially modified joystick of the preferred vision testing device implementing the present method which is used by the subject for responding to the foveal image as well as the radial location of the peripheral target.
Figure 3B:
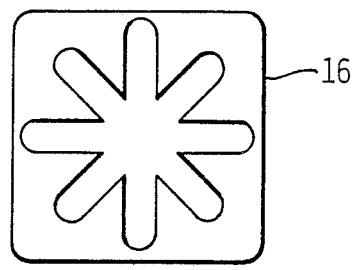

FIG. 3 illustrates joystick 4 which a subject will use to respond to the displayed images of the present method. Two buttons 15 are located on the base of joystick 4 from which the subject is to select and respond to the foveal image 12 (for example, a happy or sad face). These two buttons 15 are labeled for ease in responding. The number of buttons 15 is not limited to two, and may be increased in other embodiments.

Movement of the joystick 4 is restricted to eight possible locations (0°, 45°, 90°, 135°, 180°, 225°, 270° and 315°). A metal plate 16 shown in FIG. 3b has a cutout to restrict the movement of the joystick 4 to the eight locations. The metal plate 16 will be inserted inside the joystick mechanism.

Figure 4:
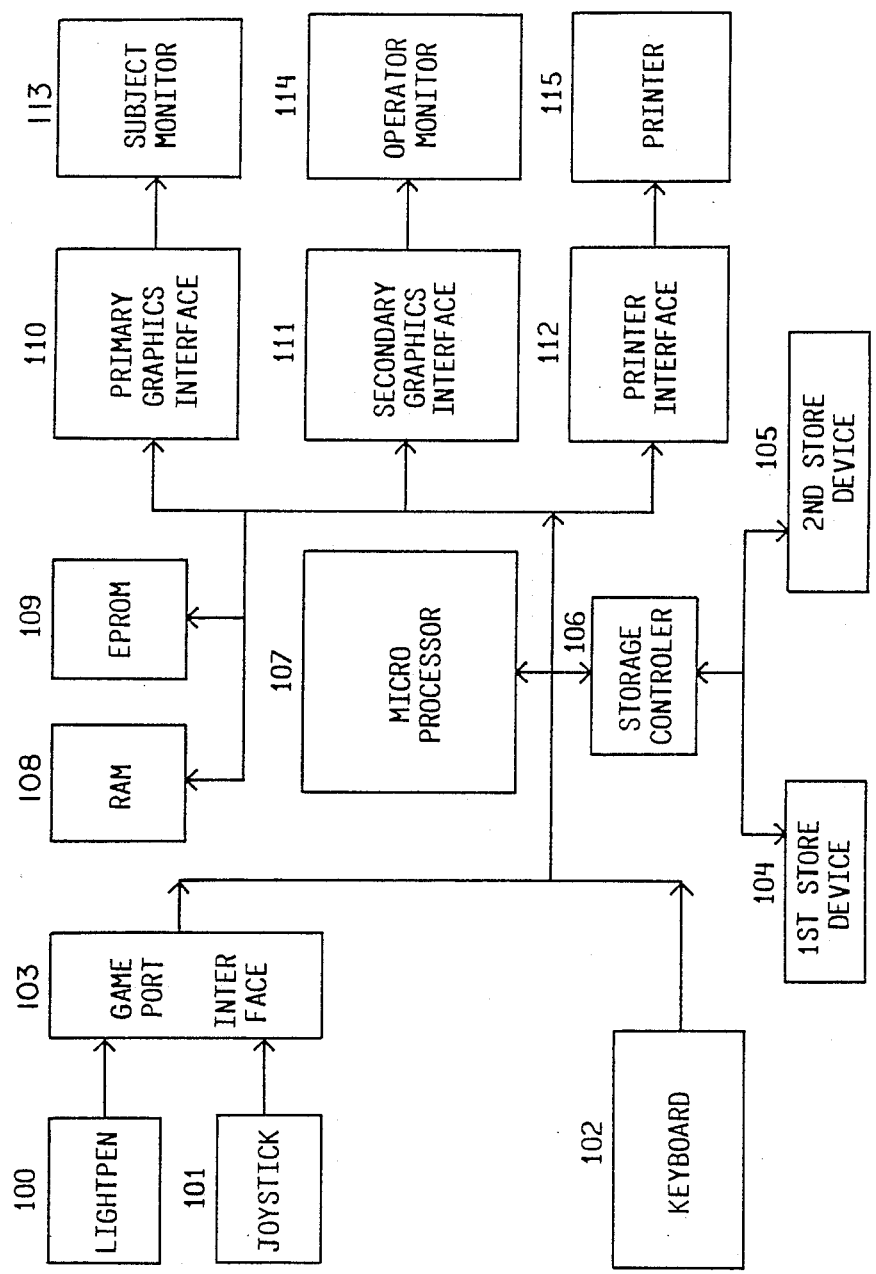
FIG. 4 is a circuit block diagram of the preferred automated vision testing device implementing the present method.
Figure 5:
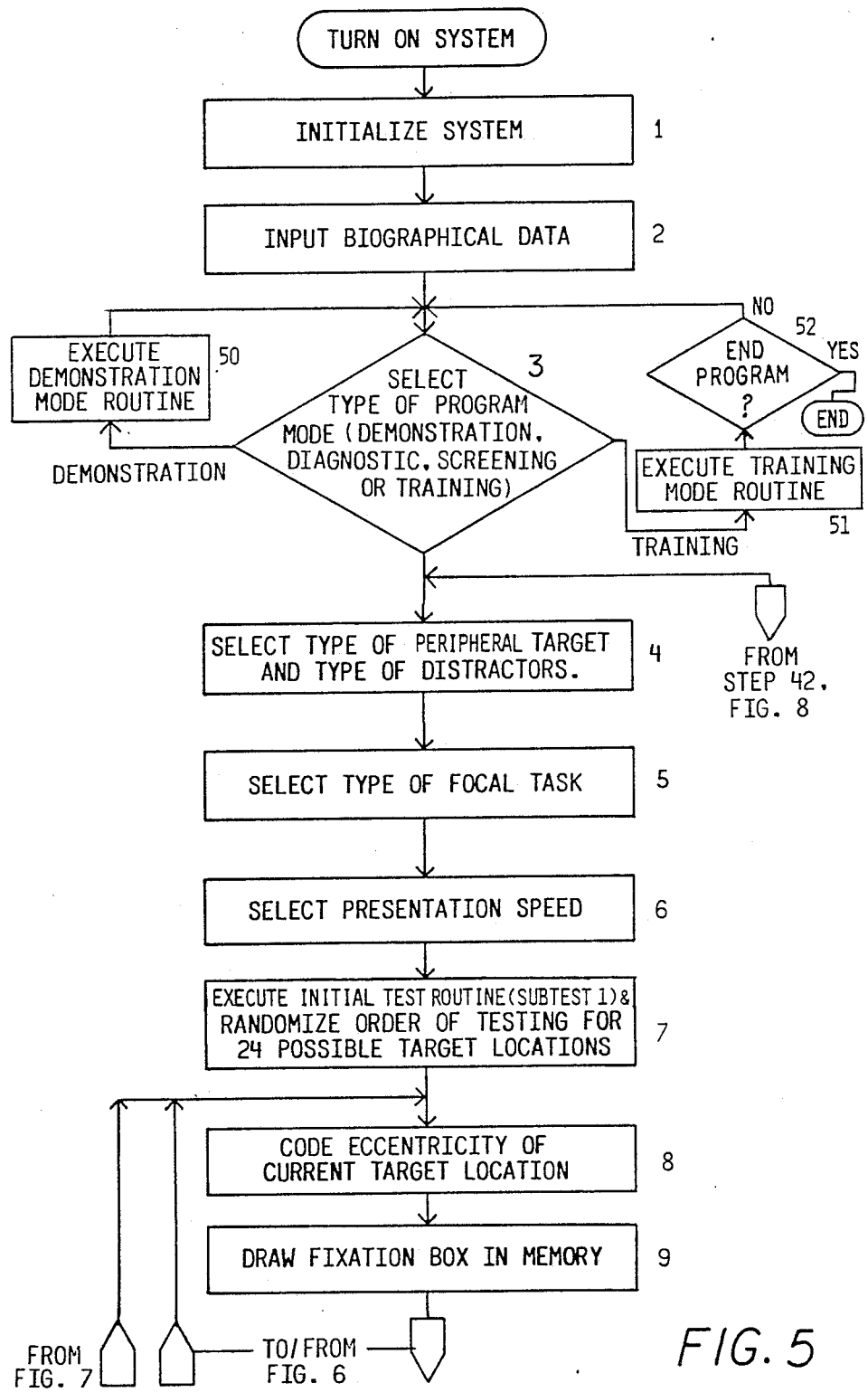
FIGS. 5-8 are a flowchart describing the processing sequence of a preferred testing device implementing the present method for measuring, diagnosing and training a subject's UFOV.
Figure 6:
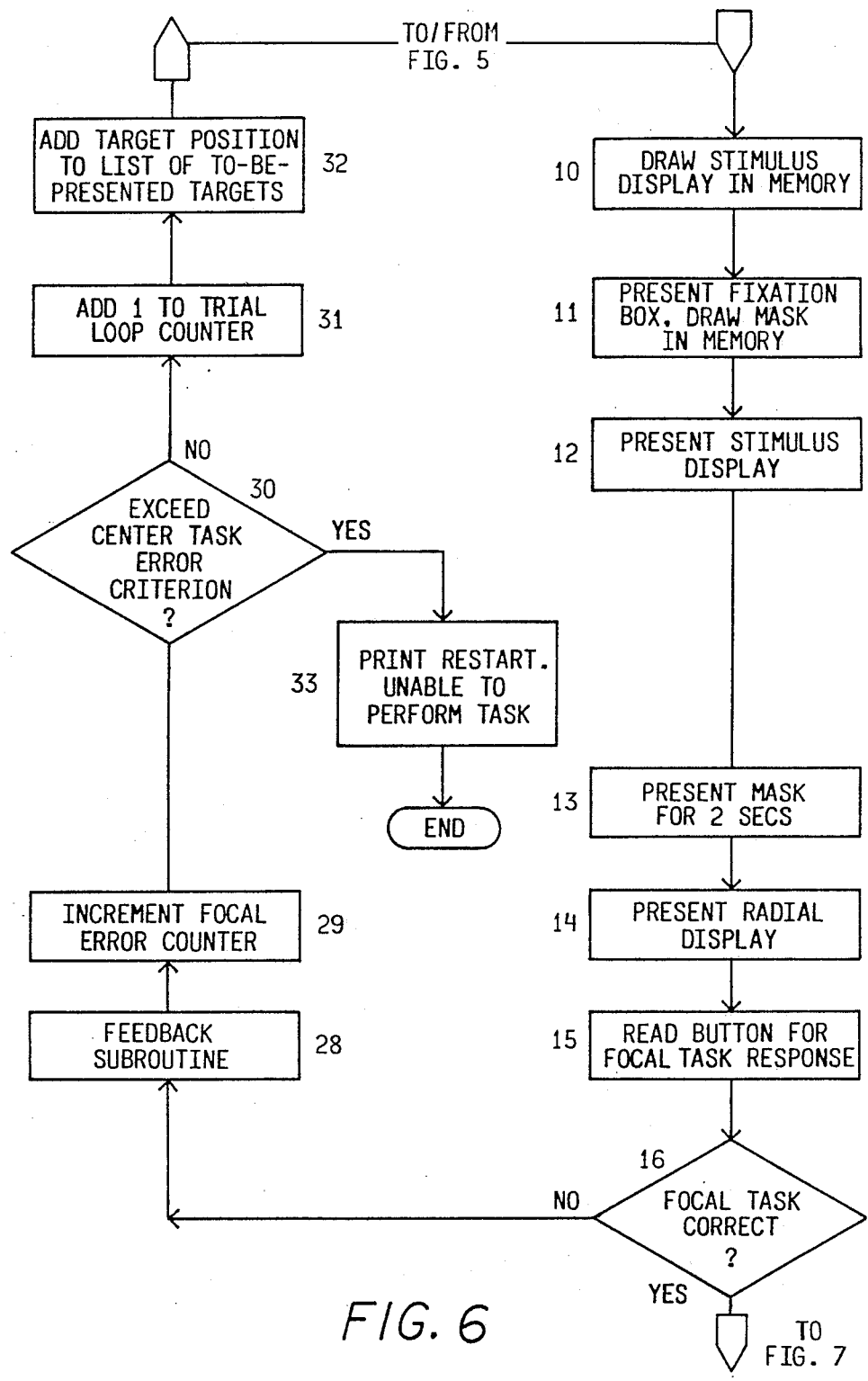
Figure 7:
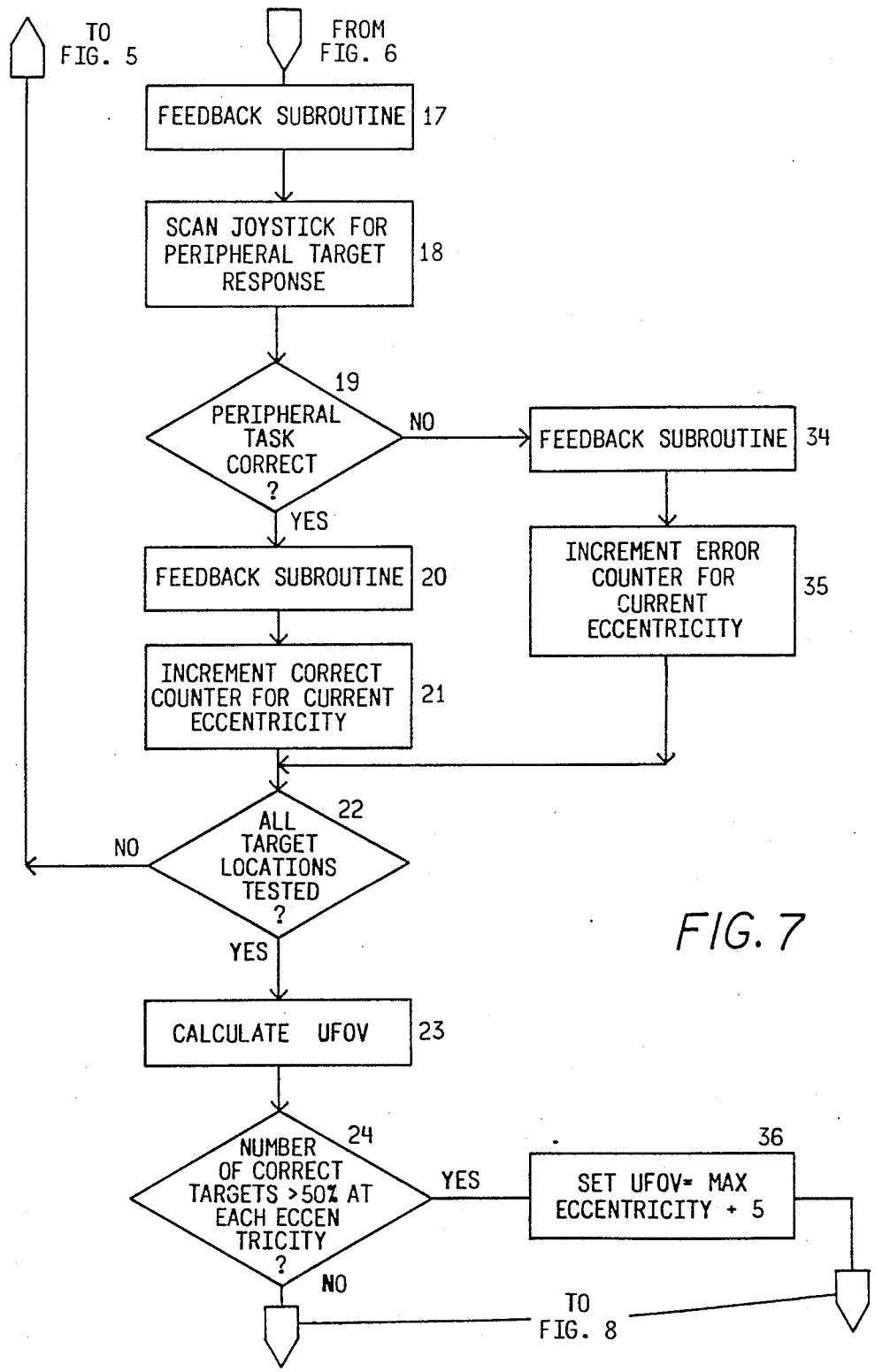
Figure 8:
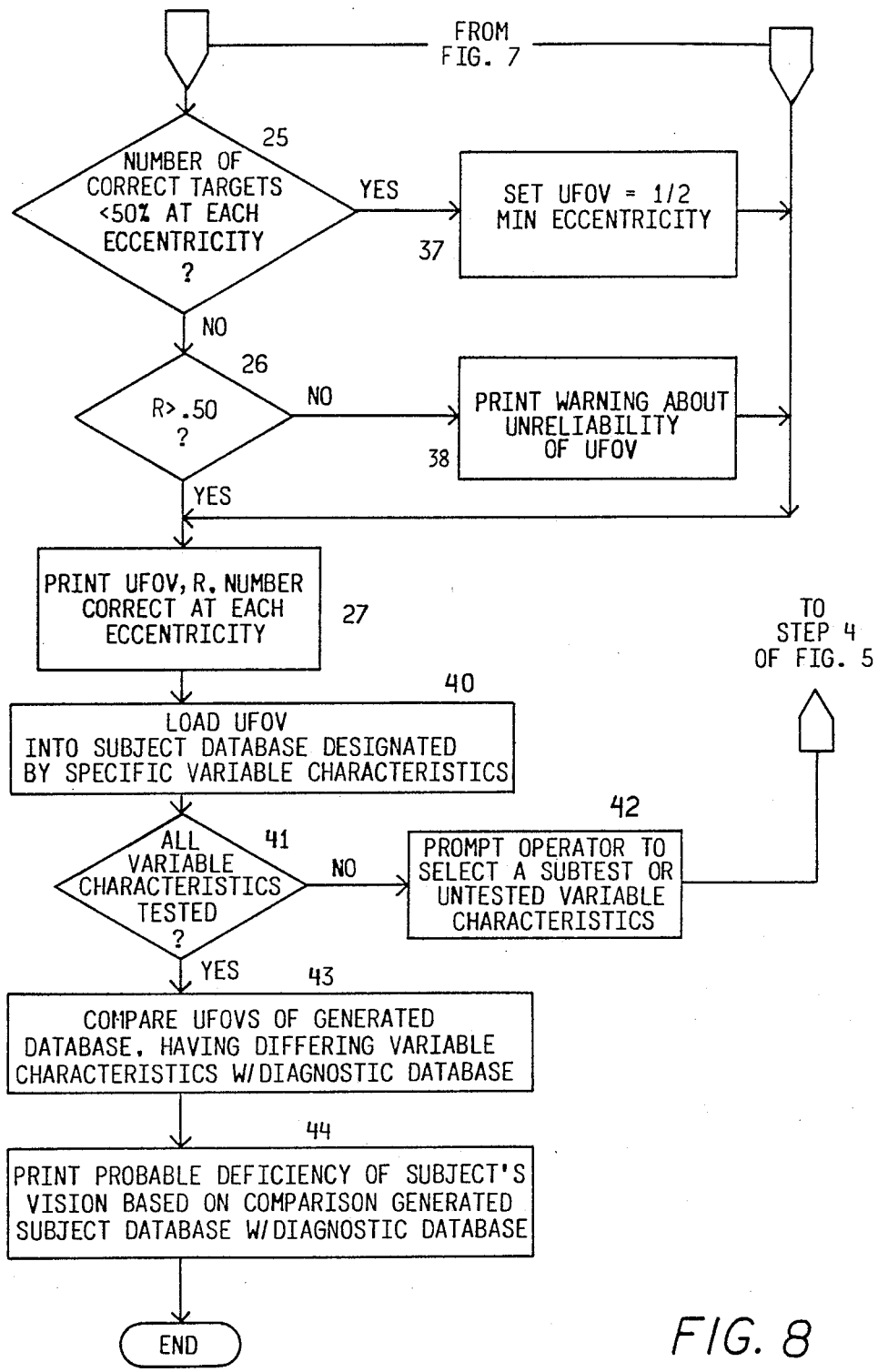

FIG. 4 is a circuit block diagram of a preferred embodiment implementing the present method. The microprocessor 107 in this preferred embodiment is an 80-86 with a clock speed of 12.5 MHz. Microprocessor 107 is available from several vendors but the preferred source would be Intel, Inc. The circuitry for this system will be centralized around the motherboard which is manufactured by Western Digital Corp. The basic system may be purchased from SAI Systems Laboratory, Inc., 911 Brigeport Avenue, Sheldon, Conn. 06484. These components will include: a vertical case, Western Digital AT-12.5 MHz motherboard with a Phoenix Bios, 512K memory, 32K cache memory, 2 serial ports, one parallel port, one mouse port, clock calendar with battery backup, five unused expansion slots, 200 watt power supply, 1.2 MB floppy drive and a 40 MB Seagate hard disk drive.

Eprom chip 109 stores the program executed by the foregoing hardware for implementing the present method. Ram chip 108 stores temporary data. The storage controller 106 assimilates the data for proper storage on the first storage device 104 which can be the Seagate hard disk drive and a second storage device 105 which can be the 1.2 MB floppy drive as described above. First storage device 104 is used to store pertinent patient information relating to test results. Second storage device 105 is for the purpose for acquiring backup copies of data in the event of a hard disk failure.

The system operator can input data via two means. The light pen 100 can be touched to the operator monitor 114 to input data to the system. The operator monitor 114 model MC-1000 is manufactured by the FTG Corp. in Scranton, Calif. Data from the light pen 100 and the joystick 101 flows through the game port interface 103, much like the Gravis Switchable Game Control Adaptor. The joystick 101 is similar to a Craft Model KC 3, but it is modified so that it can only move to eight locations. The subject inputs data into the system via the joystick 101. The keyboard 102 which interfaces directly with the motherboard is a secondary system operator input device and affords the system operator optional input methods.

The two monitors utilized to implement the present method, the subject monitor 113 to be viewed by the subject or patient and the operator monitor 114, each have their own interface card. The subject monitor 113 is approximately 20 inches diagonal. There are several monitors available, but the preferred embodiment employing the present method for diagnosing a subject's vision utilizes the NEC Multisync Model 5D which has resolution capabilities of 1280 by 1024. The NEC monitor has a video graphics adaptor similar to the VGA Wonder Advance from Technologies Incorporated. The interface has a video memory of 512K and allows intense graphic manipulation. The operator monitor 114 in a preferred embodiment is a 7 inch diagonal monochrome similar to the Zenith Model DJ7NK2. The secondary graphics interface 111 for operator monitor 114 may be a conventional monochrome graphics adaptor. Printer 115 is preferably a typical thermal printer and the interface 112 for this device is a common RS232 serial card.

FIGS. 5-8 illustrate a flowchart of the structure of the program executed by the foregoing hardware to implement the present method. After turning on the device, steps 1-7 indicate how the system initializes, prompts the system operator to input data on the subject or patient, and then requests the system operator to select all the initial parameters and then execute initial test routines. The system operator then selects the type of mode (i.e., demonstration, screening, or training). If the demonstration mode is selected in step 3, the system goes to step 50 and aquaints the subject with the types of various stimuli used as the foveal image and also permits the subject to experiment with a practice test. After executing the demonstration mode, the system returns to step 3. If the training mode is selected in step 3, the system goes to step 51 and permits the subject to experience longer blocks of trials at a single or at various time duration periods. After executing the training mode, the system operator may exit the system in step 52 or return to step 3.

If the system operator selects the screening mode in step 3, the system will measure the UFOV and diagnose the subject's visual system. The system operator may use the routine already set up in the system, or customize a routine if desired. If desiring to customize a screening procedure, the system operator must then select the type of computer generated peripheral target 13 (i.e., human face, stop sign, pedestrian, automobile, airplane, etc.) and peripheral distractors 14 (i.e, geometric shapes, human faces, traffic signs, pedestrians, automobiles, etc.). It is important for the system operator to remember that the chosen peripheral target 13 and chosen distractors 14 must be perceptually distinct so that the subject can distinguish between the two. (See FIG. 2b.) Distinctions between the peripheral target 13 and distractors 14 may be achieved by varying such characteristics as type, intensity, luminance, size, and the like.

After selecting the combination of peripheral target 13 and distractors 14, the system operator must select the foveal image 12 and time duration period of the visual stimulus 2b. Several foveal images are available to chose from and each varies in difficulty. For example, the subject may be asked to detect the presence of a foveal image 12, determine whether or not some characteristic of the foveal image 12 is present or how many stimuli are presented in the fixation box 11. Duration periods are measured in terms of a number of predetermined time-delay cycles within a delay routine of the system. Duration periods typically range from about 10 to 200 milliseconds, with the discerning difficulty of the foveal image 12 increasing with the presentation speed. The choice of the duration period is dependent upon the type of peripheral target 13 and distractors 14 combination, age of the subject and other factors.

In accordance with the present method, the characteristics of the peripheral target, distractors, foveal image, and duration period are varied with each block of trials presenting a plurality of times the set of four sequentially displayed images of FIG. 2. The varying of the specific characteristics of each block of trials provided in the present method enables the system operator to make a diagnosis of the subject's vision by creating a subject database that records the subject's indicated responses to each block of trials and comparing this subject database to a normative diagnostic database. Each block of trials gives a UFOV value. The values of UFOV for all the blocks are used collectively to make a diagnosis using normalized UFOV values as a basis for comparison.

The peripheral target 13 of each set of four sequentially displayed images may appear in any of 24 possible locations: the locations are defined by the intersection of eight (8) radial spokes and three (3) eccentricities 20. (See FIGS. 2b and 2d.) The three eccentricities 20 typically have a visual angle radius of 10°, 20° or 30° from the fixation point of subject, and the eight radial spokes are arranged at 0°, 45°, 90°, 135°, 180°, 225°, 270°, and 315°. Only one position is tested on each trial and the remaining positions as well as the area between the positions, are filled with distractors 14. This results in a display which has one peripheral target 13 and forty-seven distractors 14. Each of the 24 potential peripheral target locations is randomly tested. However, the present method is such that no peripheral position is tested twice within a block of trials. The initial test routine of step 7 (or subtest 1) determines processing speed by only presenting foveal images for differing durations of time.

Step 8 is the beginning of the main portion of the screening mode. A peripheral target position is selected from the randomizing order of step 7. The position of the peripheral target 13 is then coded into temporary variables. In step 9 a fixation box, having a visual outline subtending 8° vertical by 9° horizontal of visual angle is loaded into memory. In step 10 the display described in step 7 is loaded into memory. The appropriate peripheral target 13 is then set in the predetermined peripheral position with the distractors 14 in the remaining positions. The appropriate foveal image 12 is also drawn.

Figure 2A:
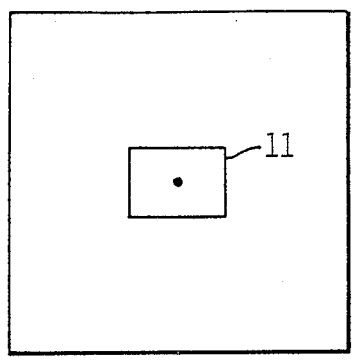
FIG. 2 illustrates the set of four sequentially displayed images of the present method having variable characteristics utilized in measuring, diagnosing and training a subject's UFOV.
Figure 2B:
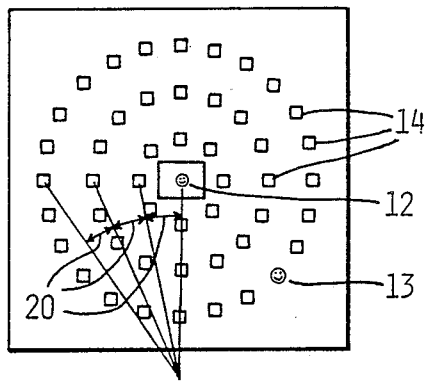
Figure 2C:
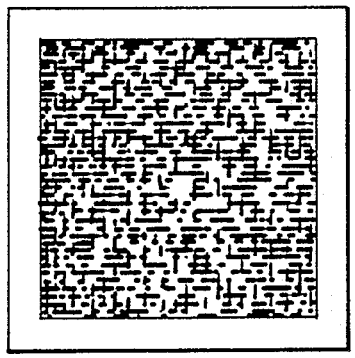
Figure 2D:
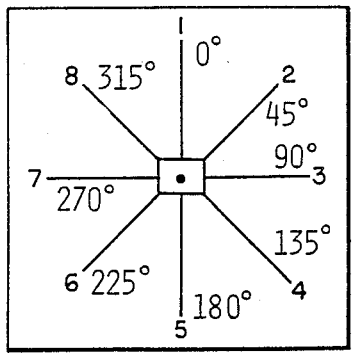

In steps 11–16 the visual stimuli of the method, as illustrated in FIGS. 2a–2d, are displayed in sequence on the subject monitor 3 with FIG. 2d remaining on the subject monitor 3 until the subject responds via the joystick 4. As provided by the present method, the characteristics of each block of trials displaying a plurality of times a set of four sequentially displayed images are altered with each new block of trials to enable a diagnosis to be made.

If the subject responds incorrectly in discerning the foveal image 12 in step 16, then the system goes to step 28 in which the system audibly signals an incorrect response and then in step 29 increments the foveal discerning error counter. The system also checks to see if the foveal discerning error criterion has been exceeded. Usually the criterian is about 12–15 foveal discerning errors. In step 30 the system checks to see if the number of errors has exceeded this amount, and if so, goes to step 33 in which printer 9 prints a warning message that the subject is unable to discern the foveal image 12. If the foveal discerning error criterion has not been exceeded, then the system goes from step 30 to step 31 in which the trial loop counter is incremented by 1 and the peripheral target location is added to the lists of possible future locations to be presented targets in step 32. The system then returns to step 8 in which the visual stimulus sequence of FIGS. 2a–2d is repeated.

Returning to step 16, if the subject correctly discerns the foveal image 12, then the system audibly signals a correct response in step 17 and awaits a signal from the joystick 4 indicating the subject's perceived peripheral target location in step 18. In step 19 the system determines if the selected peripheral target location is correct. If incorrect, the system goes to step 34 in which an audible sound signals an incorrect response and then goes to step 35 in which the error counter for that particular eccentricity is incremented. If the correct location of the peripheral target 13 is selected, then the system audibly signals a correct response in step 20 and increments the correct counter for the current eccentricity in step 21. After determination of whether the correct peripheral location has been selected, the system goes to step 22 in which a determination is made as to whether all the peripheral target locations have been tested. If not, the system returns to step 8 and repeats the visual stimuli of FIG. 2a–2d. If the system determines that all the peripheral target locations had been tested in step 22, then the system goes to step 23 in which it calculates the UFOV.

The algorithm of the present method used in calculating the UFOV consists of first calculating the slope, intercept and correlation of the best fitting line between the target eccentricity and the number of correctly located peripheral targets at each eccentricity using standard regression techniques. The estimated UFOV is equal to the predicted eccentricity at which peripheral targets are localized correctly 50% of the time.

The hardware system implementing the present method determines in step 24 if the number of correctly localized peripheral targets is greater than 50% at each eccentricity. If the number is greater than 50% at each eccentricity, then the system goes to step 36 in which it sets the UFOV equal to the maximum eccentricity plus five degrees. If the number of correctly localized peripheral targets is not greater than 50% at step 24, then the system goes to step 25 in which it determines whether the number of correctly localized peripheral targets is less than 50% at each eccentricity. If the number of correctly localized peripheral targets is less than 50% at each eccentricity, then the system goes to step 37 in which it sets the UFOV equal to ½ the minimum eccentricity.

However, if the system determines in step 25 that the number of correctly localized peripheral targets is not less than 50% at each eccentricity, then the system goes to step 26 in which it will determine if the correlation calculated in step 23 is greater than 0.5. If the correlation is not greater than 0.5, than the system goes to step 38 in which a warning will be printed about the unreliability of the UFOV.

If the correlation calculated in step 23 is greater than 0.5, then the system goes to step 27 and prints the number of correctly discerned foveal images, the number of correctly localized peripheral targets at each eccentricity, the correlation calculated in step 23, and the estimated UFOV. After step 27, the method program in step 40 will load the UFOV into the subject database and designate that UFOV by the specific variable characteristics used in calculating that specific UFOV.

As provided by the present method, in step 41 the system determines if all the variable characteristics for each block of trials to be used in diagnosing the subject's vision have been tested. The characteristics for each block of trials will have been previously determined based on the characteristics for each block of trials that are necessary to accurately diagnose a subject's vision. As set out by the method of this invention, the results of these tested variable characteristics creating a subject database will be compared (either manually or automatically) to a set of diagnostic variable characteristics forming a diagnostic database. Each set of diagnostic variables represents a characteristic of a visual function, either normal or deficient. By comparing these two databases, a diagnosis of the subject's vision revealing possible deficiencies can be made.

Thus, if some variable characteristics remain untested in step 41, the system will prompt the operator in step 42 (or it can be automatic) to select a new variable characteristic and return to step 4. Once all variable characteristics are tested, the system will compare the created subject database and the diagnostic database in step 43, and print probable deficiencies of the subject's vision in step 44. After step 44, the method examination cycle will end.

The following is a description of an exemplary embodiment of a particular diagnostic routine according to the foregoing screening mode. As discussed above in the present method, the screening mode enables the system operator to diagnose the subject's vision by presenting blocks of trials having specific variable characteristics. By varying the characteristics of each block of trials, a diagnosis can be made by comparing the results of the subject's responses to the visual stimuli with "normative" (or standardized) responses.

The particular diagnostic routine consists of a series of 5 subtests. The following is an outline of the order and type of testing, as well as how each of the tests is compared to arrive at a diagnosis.

Subtest 1: This subtest consists of a stimulus presentation of the foveal image 12 only and is executed by the system at step 7 of the flowchart. This subtest is intended to set up the initial timing conditions for the main portion of the screening mode as set forth in FIG. 6–8 and subtest 2–5 as follows.

During the presentation of the simpler to discern of the two foveal images 12, the subject views a two-lane road (located in the fixation box), and the subject is asked to indicate whether an automobile positioned on this road is in the left or the right lane. The order of presentation (left or right) is random. The more difficult to discern foveal image 12 consists of two vehicles present on the road (either an automobile and a bicycle, or an automobile and a truck) and the subject will again be asked to indicate whether the automobile is in the right or the left lane. Subjects indicate their choice by pushing either the right or the left button 15 located on the joystick 4.

These two types of stimuli are presented in random order to test simultaneously the time duration periods of display required to make the correct decision 75% of the time for each task. The duration period required to achieve 75% correct on the simpler to discern of the two foveal images 12 is designated as T1. The duration period required to achieve 75% correct on the more difficult to discern of the two foveal images 12 is designated as T2. These duration periods T1 and T2 are determined by using a tracking procedure in which the stimulus duration period starts out at 208 milliseconds and is decreased by 16 milliseconds for every two consecutive correct decisions and increased by 16 milliseconds for every incorrect decision. The duration period corresponding to 75% correct is calculated by averaging the last 8 reversals in duration for that particular task in a series of 10 reversals.

Subtest 2: This subtest consists of a stimulus presentation including both the simpler to discern of the two foveal images 12 (as described above) and a peripheral target 13. This subtest consists of localizing a peripheral target 13 (stop sign) which is presented in isolation (i.e., no distractor elements are present). This subtest uses the duration period T2 obtained on subtest 1 and consists of 24 trials with the peripheral target 13 presented once in each potential position as described earlier (3 eccentricities×8 radial locations). This subtest yields two measurements:(1) the number of correctly discerned foveal images 12 with an easy to distinguish peripheral target 13, and (2) the size of the UFOV with no distractors 14, an easy to discern foveal image 12, and duration period T2.

Subtest 3: This subtest is the same as subtest 2 except that the stop sign will be embedded in a set of 47 distractor elements to make it less conspicuous. It calculates two measurements as well: (1) the number of correctly discerned foveal images 12 with a more difficult to distinguish peripheral target 13, and (2) the size of the UFOV with distractors 14, easy to discern foveal image 12 and duration period T2.

Subtest 4: This subtest is the same as subtest 3 except it uses duration period T1, rather than T2, to calculate the UFOV when the visual stimuli is more quickly presented. The two measurements calculated are: (1) the number of correctly discerned foveal images 12 with the more difficult to distinguish peripheral targets 13, and (2) the size of the UFOV with distractors 14, easy to discern foveal image 12 and duration period T1.

Subtest 5: This subtest is the same as subtest 4 except that it uses the more difficult to discern foveal image 12 as described in subtest 1, and is presented for a duration period T2. The two measurements calculated are: (1) the number of correctly discerned foveal images 12 which are more difficult to discern while having to distinguish a more difficult peripheral target 13, and (2) the size of the UFOV with distractors 14, difficult foveal image 12 and duration period T2.

Following completion of the five subtests the following comparisons are made in step 43 of the screening mode:

1. T2-T1 with no peripheral target as calculated in subtest 1. This provides a measurement of the difference in duration periods required for the simple and more difficult to discern foveal images 12. A large difference in duration periods, relative to age norms for these particular tests indicates difficulty with cognitive complexity.

2. By comparing the number of foveal discerning errors on subtests 1, 2, and 3 it is possible to measure the effect of localizing the peripheral target 13 on the observer's ability to discern the simpler foveal image 12. If the addition of the simple and then more difficult to distinguish peripheral target 13 causes a marked decline in the performance of discerning the foveal image 12 relative to the 75% correct obtained in the first subtest, it indicates a divided attention problem.

3. By comparing the number of foveal discerning errors on subtests 1 and 5 it is possible to measure the effect of localizing the peripheral target 13 on the subject's ability to discern the more complex foveal image 12. A large effect here also indicates a divided attention problem.

4. A comparison of the size of the UFOV obtained in subtests 2 and 3 provides a measure of the effect of distractors 14. The comparison here is on distinguishing the peripheral target 13. A measurement is calculated to indicate the degree of shrinkage of the UFOV with distractors 14. This measurement is indicative of a subject's inability to focus attention or ignore irrelevant information in the visual field. Typically this is a much greater problem among older individuals in general than younger ones.

5. A comparison of the size of the UFOV obtained in subtests 3 and 4 provides a measurement of the effect of duration periods. The comparison here is again on distinguishing the peripheral target 13. A measurement is calculated which indicates the degree of shrinkage of the UFOV as the duration period of the visual stimuli is increased. A large effect here indicates slowing in the speed of processing between the eye and the brain.

6. A comparison of the size of the UFOV obtained in subtests 4 and 5 provides a measurement of the effect of increasing the difficulty in discerning the foveal image 12 on the size of the UFOV. A large effect here indicates shrinkage in the visual field due to difficulty in dividing attention between foveal and peripheral vision.

As stated earlier, values obtained in the five subtests and the resulting comparisons are to be compared to normative data (age-matched individuals with no evidence of clinical pathology). By making these comparisons it is possible to calculate relative losses for a given individual. For example, Individual 1 may be 50% slower in the speed of visual/cognitive processing than others of his age group (comparison 5). Applicant has found that individuals with this result typically report the following types of everyday problems.

1. Trouble noticing objects off to the side. 2. Trouble seeing moving objects coming from the side until they are right in front.
3. Trouble noticing things in peripheral vision.
4. When driving at night, objects from the side unexpectedly appear or pop up in field of view.
5. When driving, other cars surprise subject from the side, due to not noticing them until the last moment.
6. Long fixation time before recognizing objects.
7. Problems judging how close or far things are.
8. Trouble finding things in a dimly lit room.
9. Trouble reading the credits at the end of a movie as they move up the screen, because they move too fast.
10. Taking a long time to find an item in an unfamiliar store.
11. Taking a long time to get acquainted with new surroundings.
12. Finding that visual information (for example, TV weather information and sports results) is presented too rapidly.

If the problem appears to be solely one of slowing, and distractor and divided attention problems are minimal, a particular type of training would be recommended (described hereinafter).

By comparing localization performance both with and without the distractors 14 a measure of distractor effect was obtained in comparison #4 above. This problem could be due to a blurring of the image (possibly due to cataract) or some other optical problem that is making the target less distinct. If optical problems can be ruled out and the distractors 14 are causing more of a problem than for other individuals of the same age group, then the individual is experiencing greater than average difficulty in ignoring irrelevant information in the visual field. Applicant has found that individuals with this result typically report the following types of everyday problems:

1. Trouble reading the price tags on supermarket shelves or on the item itself.
2. Difficulty reading small print under poor lighting.
3. Problems locating something when it's surrounded by a lot of other things.
4. Reading the dials and directions on appliances (for example, washing machine, stove) when the room is not well lit.
5. When driving, other cars surprise subject from the side, because not noticing them until the last moment.
6. Difficulty focusing on things at a distance after reading or doing close-up work.
7. Trouble driving when there are headlights from oncoming cars in the field of view.
8. Trouble seeing moving objects coming from the side until they are right in front.
9. Taking a long time to find an item in an unfamiliar store.
10. Trouble locating a sign when it is surrounded by a lot of other signs.
11. When driving at night, objects from the side unexpectedly appear or pop up in subject's field of view.
12. Problems carrying out activities that require a lot of visual concentration and attention.
13. Trouble finding a person when he/she is in a group of people.
14. Trouble finding a specific item on a crowded supermarket shelf.

If the problem appears to be solely one of distractors 14, and significant slowing and divided attention problems do not exist a different training program (to be described later) would be implemented.

By comparing localization performance with varying degrees of demand required in the center task a measure of cognitive load is obtained in comparison #6 above. This problem is due to the inabiliby of subjects to attend to both the central and peripheral components of the task at the same time. By increasing the discerning difficulty of the foveal image 12, the UFOV is reduced, resulting in an inability to see targets in the periphery. Applicant has found that individuals with this result typically report the following types of everyday problems.

1. Problems carrying out activities that require a lot of visual concentration and attention.
2. When driving, other cars surprise subject from the side, due to not noticing them until the last moment.
3. Trouble seeing moving objects coming from the side until they are right in front.
4. Trouble following TV programs in which scenes change rapidly.
5. When driving at night in the rain, subject has difficulty seeing the road because of headlights from oncoming cars.

If the problem appears to be due to an inability to divide attention, but significant slowing and distractor problems do not exist, a different training program would be implemented.

The following is a description of an exemplary training mode. As discussed above, the training mode enables a subject to improve his or her UFOV by practicing specific areas of the visual stimuli tests in which the subject was deficient.

1. Problem due to reduced speed of processing of visual/cognitive information.

In this case a tracking procedure is initially used to determine the duration period required for the individual to obtain 75% correct in discerning the simpler of the two foveal images 12 while concurrently localizing the peripheral target 13 with distractors 14 present in the field. Once this starting duration period is determined blocks of practice trials are provided that gradually decrease the duration period each time the calculated UFOV exceeded 30 degrees (i.e., greater than 50% correct localizations at each of the three eccentricities). This procedure is followed until the level of performance remains essentially the same for four consecutive blocks of trials or some criterion level of performance is reached.

2. Problem due to distractor effects.

In this case cataracts or poor optical correction is ruled out as the basis of the problem. A determination is made of the duration period required for the subject to correctly discern 75% of the time the simpler of the two foveal images 12 while concurrently localizing the peripheral target 13 without distractors 14 (the most salient condition). Once this starting duration period is determined, blocks of practice trials are provided that gradually decrease the salience of the peripheral target 13 each time the calculated UFOV exceeded 30 degrees. Decreasing the salience is accomplished by adding distractors 14 which become more and more similar to the peripheral target 13 until finally they differ in figural detail alone. This procedure is followed until the level of performance remains essentially the same for four consecutive blocks of trials or some criterion level of performance was reached.

3. Problem due to divided attention difficulty.

In this case a determination is made of the duration period needed for the subject to correctly discern 75% of the time the simpler of the two foveal images 12 while concurrently localizing the peripheral target 13 with distractors 14. Practice trials are then provided at that duration period until the subject exceeds the UFOV criterion of greater than 30 degrees. The discerning complexity of the foveal image 12 is then increased providing additional practice until the subject can discern the more complex foveal image 12 at an equivalent level of discerning the simpler of the two foveal images 12.

I claim:

1. In a system for measuring and diagnosing a subject's useful field of view (UFOV), a method comprising the steps in the sequence set forth:
    (a) positioning the subject before a display screen;
    (b) displaying a fixation box on a display screen to position the subject's foveal view;
    (c) displaying a foveal image on the display screen located at the center of the fixation box wherein the foveal image has a first level of discerning difficulty, superimposing on the display screen a peripheral image over the foveal image wherein the peripheral image has distractor stimuli positioned at a plurality of possible eccentricities and radial locations from the foveal image such that each of the positions is outside of the foveal view of the subject derived from focusing on the foveal image, and having a peripheral target in the peripheral image that has a first level of distinguishing difficulty from the distractor stimuli and wherein the peripheral target is located at one of the plurality of possible eccentricities and radial locations from the foveal image;
    (d) removing the foveal image and peripheral image from the display screen after a first duration period and displaying on the display screen a masking image intended to suppress any afterimage created on the subject's retina after removal of the foveal image and peripheral image;
    (e) displaying on the display screen a prompt image for prompting the subject to indicate details of the foveal image and correct radial location of the peripheral target in relation to the foveal image as perceived by the subject;
    (f) recording accuracy of subject's perceived details of the foveal image and the radial location of the peripheral target as indicated by the subject; and
    (g) repeating steps (b)–(f) varying the eccentricities of the peripheral target, radial location of the peripheral target, details of the foveal image, discerning difficulty of the foveal image, distinguishing difficulty of the peripheral target, and the duration period for displaying the foveal and peripheral images in order to create a database of subject's perception ability.
    (h) correlating the database with normative data to diagnose the subject's UFOV and identify deficiencies in the subject's visual system.

2. A method for measuring and diagnosing a subject's UFOV as referred to in claim 1, wherein a set consists of steps (b) through (f) of claim 1.

3. A method for measuring and diagnosing a subject's UFOV as referred to in claim 2, wherein a block of trials consists of repeating sets a plurality of times and in each block of trials only varying the eccentricities of the peripheral target, radial location of the peripheral target and details of the foveal image so as to calculate the subject's UFOV for each block of trials.

4. A method for measuring and diagnosing a subject's UFOV as referred to in claim 3, wherein the discerning difficulty of the foveal image, distinguishing difficulty of the peripheral target, and duration of time period for displaying the foveal and peripheral images are varied for each block of trials so as to diagnose a subject's vision.

5. A method for measuring and diagnosing a subject's UFOV as referred to in claim 1, wherein the radial location of the peripheral target in relation to the foveal image is one of eight alternatives consisting of 0°, 45°, 90°, 135°, 180°, 225°, 270° and 315°.

6. A method for measuring and diagnosing a subject's UFOV as referred to in claim 1, wherein the level of distinguishing difficulty of the peripheral target is altered by varying color, intensity, and design of the peripheral target in relation to the distractor stimuli.

7. In a system for improving a subject's processing speed of visual information, a method comprising the following sequential steps:
    (a) focusing the subject's vision on a fixation box to position subject's foveal view;
    (b) displaying a detailed image at the center of the fixation box while simultaneously displaying a peripheral image from the detailed image as observed by the subject having distractors and a target image;
    (c) removing the detailed image and peripheral image after displaying the images for a time period;
    (d) displaying a masking image intended to suppress any afterimage created on the subject's retina after removal of the detailed image and peripheral image;
    (e) requiring the subject to identify changing characteristics of the detailed image while simultaneously locating the target image having a changing position in the peripheral image;
    (f) repeating steps (a) through (e) varying the position of the target image, characteristics of the detailed image and time period for displaying images so as to calculate a minimum time period required for the subject to correctly identify a designated percentage of times the changing characteristics of the detailed image while concurrently localizing the target image;
    (g) repeating steps (a) through (e) a plurality of times to calculate the subject's UFOV and decreasing the time period for displaying the images each time the calculated UFOV exceeds a designated number of degrees until a criterion level of performance is reached.

8. In a system for improving a subject's visual deficiencies due to distractor effects, a method comprising the sequential steps of:
    (a) focusing the subject's vision on a fixation box to position subject's foveal view;
    (b) displaying a detailed image at the center of the fixation box while simultaneously displaying a peripheral image from the detailed image as observed by the subject having a target image;
    (c) removing the detailed image and peripheral image after displaying the images for a time period;
    (d) displaying a masking image intended to suppress any afterimage created on the subject's retina after removal of the detailed image and peripheral image;
    (e) requiring the subject to identify changing characteristics of the detailed image while simultaneously locating the target image having a changing position in the peripheral image;
    (f) repeating steps (a) through (e) varying the position of the target image, characteristics of the detailed image and time period for displaying images so as to calculate a minimum time period required for the subject to correctly identify a designated percentage of times the changing characteristics of the detailed image while concurrently localizing the target image;
    (g) repeating steps (a) through (e) a plurality of times to calculate the subject's UFOV and decreasing salience of the target image each time the calculated UFOV exceeds a designated number of degrees until a criterion level of performance is reached.

9. A method for improving a subject's visual deficiencies due to distractor effects as referred to in claim 7, wherein the salience of the target image is decreased by adding distractors to the peripheral image which become more and more similar to the target image.

10. In a system for improving a subject's visual deficiency due to divided attention difficulty, a method comprising the sequential steps of:
    (a) focusing the subject's vision on a fixation box to position subject's foveal view;
    (b) displaying a detailed image at the center of the fixation box while simultaneously displaying a peripheral image from the detailed image as observed by the subject having distractors and a target image;
    (c) removing the detailed image and peripheral image after displaying the images for a time period;
    (d) displaying a masking image intended to suppress any afterimage created on the subject's retina after removal of the detailed image and peripheral image;
    (e) requiring the subject to identify changing characteristics of the detailed image while simultaneously locating the target image having a changing position in the peripheral image;
    (f) repeating steps (a) through (e) varying the position of the target image, characteristics of the detailed image and time period for displaying images so as to calculate a minimum time period required for the subject to correctly identify a designated percentage of times the changing characteristics of the detailed image while concurrently localizing the target image;
    (g) repeating steps (a) through (e) a plurality of times to calculate the subject's UFOV and increasing complexity of the detailed image each time the calculated UFOV exceeds a designated number of degrees until a criterion level of performance is reached.

* * * * *

UNITED STATES PATENT AND TRADEMARK OFFICE
CERTIFICATE OF CORRECTION

PATENT NO. : 4,971,434
DATED : November 20, 1990
INVENTOR(S) : Karlene K. Ball It is certified that error appears in the above-identified patent and that said Letters Patent is hereby corrected as shown below:

Col. 1, line 5, insert

--The United States Government has a paid-up license in this invention and the right in limited circumstances to require the patent owner to license others on reasonable terms as provided by the terms of NIA grant No. AG-05739 awarded by the United States Department of Health and Human Services National Institute of Aging.--

Signed and Sealed this

Thirteenth Day of April, 1993

Attest:

STEPHEN G. KUNIN

*Attesting Officer*        *Acting Commissioner of Patents and Trademarks*